United States Patent
Beer et al.

(10) Patent No.: US 9,719,898 B2
(45) Date of Patent: Aug. 1, 2017

(54) DEVICE FOR INSPECTING A FIBRE-COMPOSITE COMPONENT FOR CONTAMINATIONS

(75) Inventors: Sebastian Beer, Munich (DE); Andreas Helwig, Munich (DE); Gerhard Mueller, Grafing (DE); Hans Luinge, Munich (DE); Georg Wachinger, Rosenheim (DE)

(73) Assignee: EADS Deutschland GmbH, Ottobrunn (DE)

( * ) Notice: Subject to any disclaimer, the term of this patent is extended or adjusted under 35 U.S.C. 154(b) by 712 days.

(21) Appl. No.: 14/118,477

(22) PCT Filed: May 16, 2012

(86) PCT No.: PCT/DE2012/000504
§ 371 (c)(1),
(2), (4) Date: Mar. 4, 2014

(87) PCT Pub. No.: WO2012/155888
PCT Pub. Date: Nov. 22, 2012

(65) Prior Publication Data
US 2014/0190247 A1    Jul. 10, 2014

(30) Foreign Application Priority Data
May 19, 2011 (DE) .................. 10 2011 102 055

(51) Int. Cl.
G01N 1/44 (2006.01)
G01N 1/22 (2006.01)
(Continued)

(52) U.S. Cl.
CPC .............. *G01N 1/44* (2013.01); *G01N 1/2202* (2013.01); *G01N 1/2214* (2013.01); *G01N 19/04* (2013.01);
(Continued)

(58) Field of Classification Search
CPC ..... G01N 2001/028; G01N 2021/8472; G01N 33/0031; G01N 2223/501; G01N 2223/615; G01N 2223/652; G01N 1/44; G01N 1/2214; G01N 21/94; G01N 25/14
See application file for complete search history.

(56) References Cited

U.S. PATENT DOCUMENTS

| 5,425,263 | A | | 6/1995 | Davies et al. |
| 5,521,381 | A | * | 5/1996 | Gregg .................. H01J 49/04 250/288 |

(Continued)

FOREIGN PATENT DOCUMENTS

| DE | 10 2006 023 061 B4 | 8/2008 |
| JP | 2010-54498 A | 3/2010 |

OTHER PUBLICATIONS

International Search Report dated Oct. 4, 2012 w/ English translation (four (4) pages).

*Primary Examiner* — David M Gray
*Assistant Examiner* — Andrew V Do
(74) *Attorney, Agent, or Firm* — Crowell & Moring LLP

(57) ABSTRACT

A device and method for testing a fiber-composite component, which is to be processed by means of bonding, for the presence of at least one substance out of a selection of possible contaminants. A surface heating device for regional heating of a part-zone of the fiber-composite component to be bonded is performed for desorption of contaminants. A sensor array with a plurality of sensors detects contaminants in the gas phase, and a control device ascertains and signals contaminations which are found. An extractor device can be employed to extract machining dust from the fiber-composite component to a desorption device.

21 Claims, 2 Drawing Sheets

(51) Int. Cl.
  *G01N 21/94*  (2006.01)
  *G01N 25/14*  (2006.01)
  *G01N 21/3504*  (2014.01)
  *G01N 19/04*  (2006.01)
  *G01N 1/02*  (2006.01)
  *G01N 21/35*  (2014.01)

(52) U.S. Cl.
  CPC ......... *G01N 21/3504* (2013.01); *G01N 21/94* (2013.01); *G01N 25/14* (2013.01); *G01N 21/35* (2013.01); *G01N 2001/028* (2013.01); *G01N 2001/2241* (2013.01); *G01N 2223/501* (2013.01); *G01N 2223/652* (2013.01)

(56) References Cited

U.S. PATENT DOCUMENTS

| | | |
|---|---|---|
| 6,978,657 B1 | 12/2005 | Baumann et al. |
| 7,115,869 B2 | 10/2006 | Shelley et al. |
| 8,067,727 B2 * | 11/2011 | Featherby .............. G01N 21/94 250/281 |
| 8,148,691 B1 * | 4/2012 | Wong ................... G01N 21/274 250/252.1 |
| 8,302,461 B2 | 11/2012 | Angster et al. |
| 2002/0148974 A1 | 10/2002 | Hung et al. |
| 2004/0219067 A1 | 11/2004 | Ichimura et al. |
| 2005/0124074 A1 | 6/2005 | Shelley et al. |
| 2007/0275474 A1 | 11/2007 | Hartonen et al. |

\* cited by examiner

DEVICE FOR INSPECTING A FIBRE-COMPOSITE COMPONENT FOR CONTAMINATIONS

BACKGROUND AND SUMMARY OF THE INVENTION

Exemplary embodiments of the present invention relate to a device for testing a fibre-composite component, which is to be processed by means of bonding, for the presence of at least one substance out of a selection of possible contaminants and a method for operation of the device.

Repairing structural components made from fibre-reinforced plastic (FRP) by gluing joints is problematic because of the possible presence of contaminations in the plastic, which may considerably impair the bond strength of the glued joint. If, in operation, an FRP component is exposed to environmental conditions with liquid or gaseous substances which can diffuse into the plastic, this may massively impair the adhesion point and possibly result in a total failure of the adhesive joint. For this reason the adhesive bonding repair of FRP components was previously prohibited in civil aviation.

It is possible, by means of sensors such as metal oxide sensors (MOX sensors), non-dispersive infrared sensors (NDIR sensors) and/or humidity sensors to detect or even to measure the contaminants in question. This represents a very considerable expenditure only because each contaminant requires discrete sensors or sensor settings and therefore the examination for the presence of several possible contaminants is very costly both structurally and in terms of process engineering.

Exemplary embodiments of the present invention are directed to a structurally simple device that can be used in a simple and error-resistant manner by means of which a FRP component can be examined for the presence of a plurality of specific contaminants.

According to a first aspect of the invention a device for testing a fibre-composite component, which is to be processed by means of bonding, for the presence of at least one substance out of a selection of possible contaminants, wherein in a mobile integral unit this device comprises the following: a surface heating device for regional heating of a part-zone of the fibre-composite component to be bonded for the purpose of desorption of contaminants; a sensor array with a plurality of sensors for detection of all contaminants in the gas phase; a control device for regulating the surface heating device and also for activation and for readout of the sensor array and also for ascertaining and signalling contaminations which are found.

By the direct heating of a region of the surface to be treated either by means of heat conduction or heat radiation the construction according to the invention enables thermal desorption of contaminants, wherein solid or liquid phases are directly converted into the gas phase. For this purpose it is necessary for the temperature to be monitored during the process of heating of the component, to avoid unacceptably high temperatures that could damage the component. The sensor array has a sufficiently large number of sensors by which all contaminants to be to detected can be detected simultaneously, so that the testing process can be kept brief. If one or more contaminants are ascertained, a corresponding signal is optically and/or acoustically output to the user. A binary testing for the contaminants (present in critical concentration, not present) or a more precise measurement of the detected concentration can be provided, but this increases the required apparatus. An advantage of this is that it is possible to operate without a transport or carrier gas, and so the gas concentration remains undiluted, resulting in an increase in the sensitivity and the sensor speed. Furthermore the walls can be kept easily accessible for collection of the contaminants and thus cleaning and restarting the sensor can be simplified.

According to an advantageous modification of this embodiment of the invention the surface heating device is constructed as a contact heating device. In this case a heated punch is preferably provided, which is heated internally and has a sufficient thermal mass or thermal capacity, in order to effect the lowest possible temperature fluctuations during the process of heating the structural component. However, this design has the disadvantage that heating or measuring is only possible on accessible and level areas of the FRP structural component.

A modification provides that the heated punch is disposed centrally and is surrounded by the sensor array, which in turn is surrounded by an outer housing. In this way a very compact design is possible with good detection of the desorbed substances.

According to an alternative embodiment the device comprises a central heated punch that is surrounded by an annular scattered light chamber with reflecting walls, and also at least one IR light emitter is provided that radiates into the scattered light chamber and several selective photodetectors are disposed in the wall of the scattered light chamber. Both designs can also be combined, that is to say that further MOX sensors can be disposed in the scattered light chamber in addition to the NDIR sensors.

According to another modification the surface heating device is constructed as a heat radiating device. It is particularly preferable to use a halogen lamp, which can be used with lenses and mirrors for targeted irradiation of surface regions of almost any shape. In this case the temperature of the irradiated surface is measured directly, preferably by means of a radiation thermometer, wherein the radiant heat generation can be adjustable by suitable control devices as a function of the recorded temperature.

In a preferred modification of the invention the heat radiating device is disposed centrally and the sensor array is disposed around the radiation range, and an optical thermometer coupled to a control device is provided for measuring the temperature of the irradiated part-region. This structurally compact arrangement ensures that the desorbed substances remain in the detection region and can be reliably detected.

In a preferred modification of the invention the surface heating device and the sensor array can be disposed on different sides of the fibre-composite component. This embodiment has the advantage that contaminants are "pushed out" by the heat, i.e. diffuse in the matrix in a substantial part against the temperature gradients.

According to a second aspect of the invention a device for testing a fibre-composite component, which is to be processed by means of bonding, for the presence of at least one substance out of a selection of possible contaminants, includes an extractor device for extraction of machining dust from the fibre-composite component; a filter device for collecting the machining dust particles a desorption device for thermal desorption of contaminants out of the dust particles; a sensor array with a plurality of sensors for detection of all contaminants in the gas phase; a control device for regulating the desorption device, activation and for readout of the sensor array, and ascertaining and signalling of contaminations that are found.

In this embodiment there is no heating of the structural component itself, so that a thermal damage thereto can be ruled out. Instead, the milling or grinding process which is necessary before an adhesive joint is utilised in order to analyse the removed material. This construction has the advantage that a substantially larger quantity of contaminants can be desorbed by the massively enlarged surface, so that a substantially more precise detection of the contaminants is possible. Also there is no need to adhere to thermal limiting values of the structural component, it is only necessary to ensure that no thermal decomposition processes of the plastic occur that can falsify the measurement results. A disadvantage of this construction is the substantial cost of apparatus, because the machining dust must be extracted, collected and then delivered to a desorption device.

According to an advantageous modification of both aspects of the invention the sensor array comprises a number of metal oxide gas detectors (MOX), which are each sensitive for individual contaminants. These sensors are structurally simple and can be adapted to different substances to be detected.

According to an advantageous modification of both aspects of the invention the sensor array comprises at least one humidity sensor. Since the moisture content of a FRP component influences the adhesion of a bond, a high moisture content is just as harmful as contamination by special substances.

According to an advantageous modification of both aspects of the invention the sensor array comprises at least one non-dispersive infrared sensor (NDIR). A plurality of infrared sensors are preferably provided which are selective for specific frequency ranges, and of which the selectivities are adapted to the substances to be detected.

According to an advantageous modification the individual sensors of the sensor array are selective for one or more of the following contaminants (usual English names or trade names used in the aviation industry in brackets):
 surfactants (aircraft surface cleaner)
 synthetic esters (jet oil 2)
 alcohols, glycols and mixtures thereof (runway deicer)
 alcohols (developer U89)
 petrol, kerosene
 butyl phosphates, phenyl phosphates, phosphate esters (hydraulic fluids, z.B. Skydrol)
 mineral oils (turbine oil 500)
 potassium acetates, sodium formiates (Clariant safeway)
 phosphates, silicates (wet cleaner Surtec 121)
 water, moisture
 butanones, methyl ethyl ketone (MEK solvent)
 hydrocarbons, silicones, fluorocarbons (release agent)
 synthetic oils and lubricants.

According to an advantageous modification of the invention the composite component is an aircraft component. Thus, by the use of the device according to the invention, composite components in aircraft can be tested for the presence of contaminants and can optionally be repaired by bonding, which hitherto has not been allowable.

A method for testing a fibre-composite component, which is to be processed by means of bonding, for the presence of at least one substance out of a selection of possible contaminants provides for the use of the device described herein for performing an analysis of the machining dust. Thus in the grinding process for preparation of the adhesive surface the machining dust can preferably be collected and then analysed. If no contaminants are revealed, a subsequent surface analysis can either be omitted completely or can be carried out in simplified form. On the other hand, if contaminants are ascertained, a precise analysis of the substances is carried out by means of the device described herein.

BRIEF DESCRIPTION OF THE DRAWING FIGURES

The invention is explained further below on the basis of preferred embodiments with reference to the appended drawings. In the drawings.

DETAILED DESCRIPTION

Figure 1:
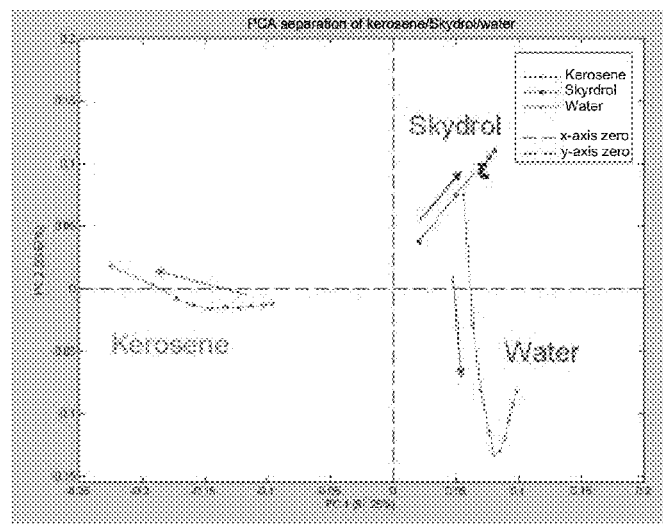
FIG. 1 shows a diagram with a principal component analysis relating to three contaminants.

FIG. 1 shows a diagram of a principal component analysis (PCA) for three contaminants frequently occurring in composite components in the aviation industry, namely kerosene, Skydrol and water, using the device proposed according to the invention. The three substances could be reliably distinguished by the use of two principal components. Kerosene can be distinguished from Skydrol and water by using principal component 1 (X axis) and Skydrol can be distinguished from water by principal component 2 (Y axis).

Figure 2:
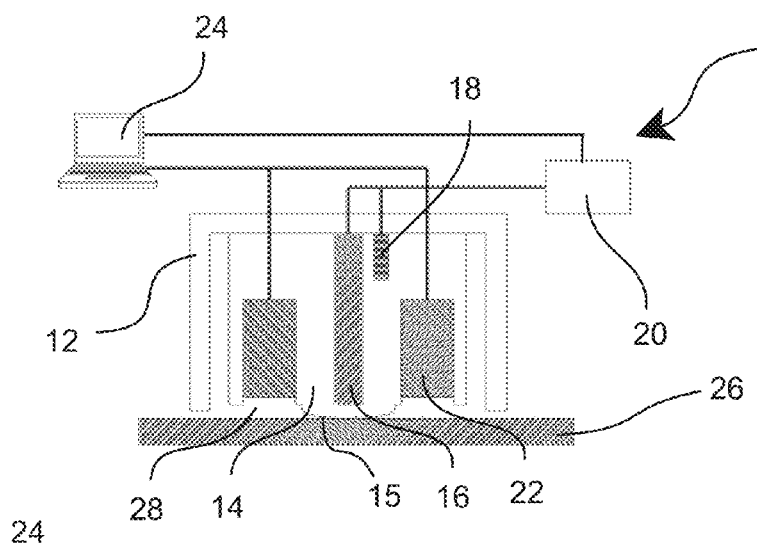
FIG. 2 shows a first preferred embodiment of an examination device.

FIG. 2 shows a first preferred embodiment of a testing device 10a in a schematic cross-section, which device consists substantially of a thermally insulating outer housing 12 in which a preferably metallic heated punch 14 is disposed centrally, wherein the punch has a heating surface 15 and can be heated internally via a heating element 16. The heating surface 15 is formed so that it can rest suitably on a composite component to be tested. In FIG. 2 the heating surface 15 has convex shape, but also a planar surface or in an individual case also a concave shape is conceivable. It is also possible to provide the heating surface 15 with a heat conductive resilient coating, in order to ensure optimal heat transfer into the interior of the composite component.

Furthermore, a thermometer 18 is disposed in the interior of the heated punch 14 and is connected together with the heating element 16 to a thermostat 20. The heated punch 14 is surrounded by an annular sensor array 22 which is coupled to a control device 24. The thermostat 20 is likewise by the control device 24 coupled.

The sensor array 22 comprises a number of MOX and/or NDIR sensors (not shown in greater detail) and preferably also a humidity sensor. The individual sensors of the sensor array 22 are configured so that they are capable of detecting a predetermined selection of contaminants.

In operation, the testing device 10a is placed onto the surface of a composite component 26 be tested so that the heating surface 15 rests on the site to be tested. By means of the heating element 16 controlled by way of the thermostat 20, the heating surface 15 and thus also the region of the composite component 26 also in contact therewith is heated to a temperature of approximately 160-220° C. (the precise temperature depends upon the material of the composite component 26 and is selected so that the material is not damaged but the most comprehensive possible diffusion and thus better detection of possible contaminants is achieved). Any contaminants present come out of the composite component 26 heated via the heating surface 15 and collect in the collecting chamber 28 on both sides of the contact surface the heating surface 15. The sensor array 22 is disposed precisely above this annular collecting chamber 28 and thus is able to detect these contaminants. For this purpose the sensor array 22 also set back somewhat relative to the heating surface 15 in order to enable the construction of the collecting chamber 28 for collecting the substances coming out of the composite material. The signals from the sensor array 22 are delivered to the control device 24, in which in particular by means of a principal component analysis (see FIG. 1) the presence or in a more complex embodiment also the concentration of contaminants is determined and corresponding optical and/or acoustic signals are output to the user.

Figure 3:
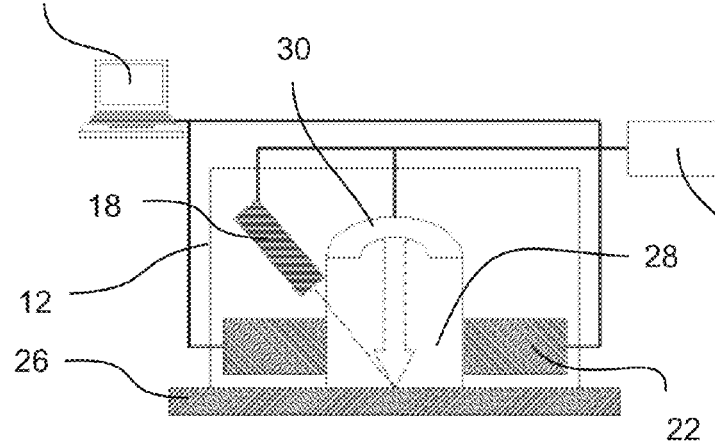
FIG. 3 shows a second preferred embodiment of an examination device.

FIG. 3 shows a second preferred embodiment of a testing device 10b in a schematic cross-section. In this case the same components as in FIG. 1 are provided with the same reference signs. This testing device 10b uses a halogen lamp 30 to generate heat in order to heat up the composite component 26. In this embodiment the thermometer 18 is a radiation thermometer that can directly measure the temperature of the heated surface so that a more precise temperature monitoring and thus a higher temperature is possible, which increases the quantity of outcoming substances and thus enables a lower detection threshold.

Figure 4:
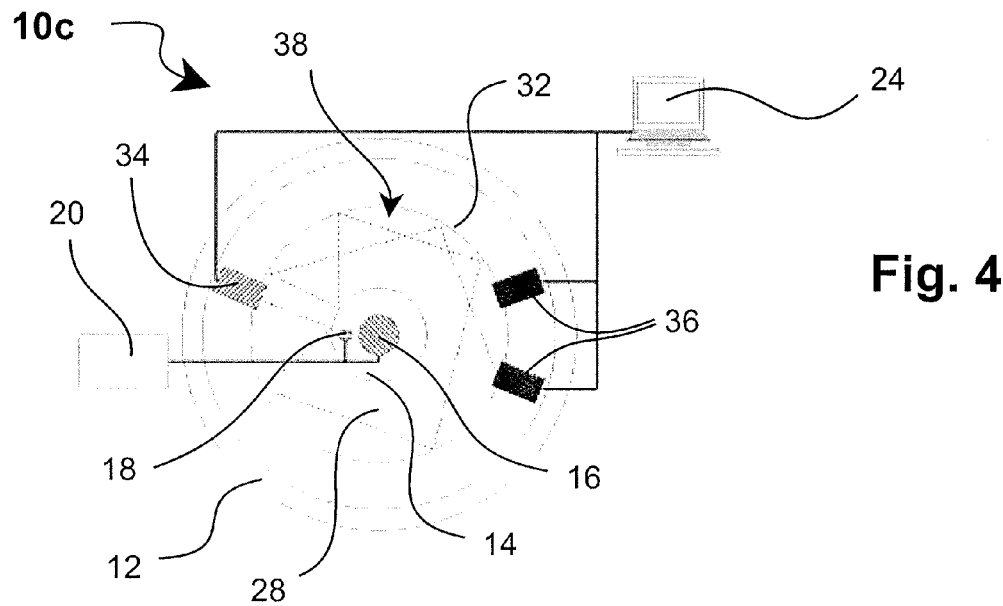
FIG. 4 shows a third preferred embodiment of an examination device.

FIG. 4 shows a third preferred embodiment of a testing device 10c in a schematic horizontal section. This is similar to FIG. 2 and likewise comprises a heated punch 14 that is heated internally by means of a heating element 16 and of which the temperature is regulated by means of the thermometer 18 and the thermostat 20. An annular scattered light chamber 28 is provided radially outside the heated punch 14 and the inner and outer walls of the chamber are designed to be reflecting. At least one IR radiation emitter 34 and a number of photodetectors 36 (for reasons of clarity only two are shown) are disposed in the outer wall 32 of the scattered light chamber 28.

In operation the heated punch 14—analogous to the construction according to FIG. 2—heats the composite component (not shown in FIG. 4) so that any contaminants present in the collecting chamber 28 escape. The scattered light chamber 28 is traversed by IR radiation 38 emitted by the IR radiation emitter 34 and reaches the photodetectors 36, being reflected several times due to the reflectivity of the inner and outer wall 32 (and the reflectivity of the upper wall which is not shown). If contaminating substances (and also other substances) are present in the scattered light chamber 28, certain spectra of the radiation are absorbed, which is ascertained by the photodetectors 36 selected by means of filters at specific frequencies or frequency bands. In practice, instead of the two shown a plurality (in particular 6 to 20) of detectors 36 will be provided, so that the individual substances can be not only detected but also selected relative to one another, as shown in FIG. 1. An unfiltered reference detector is preferably provided.

Figure 5:
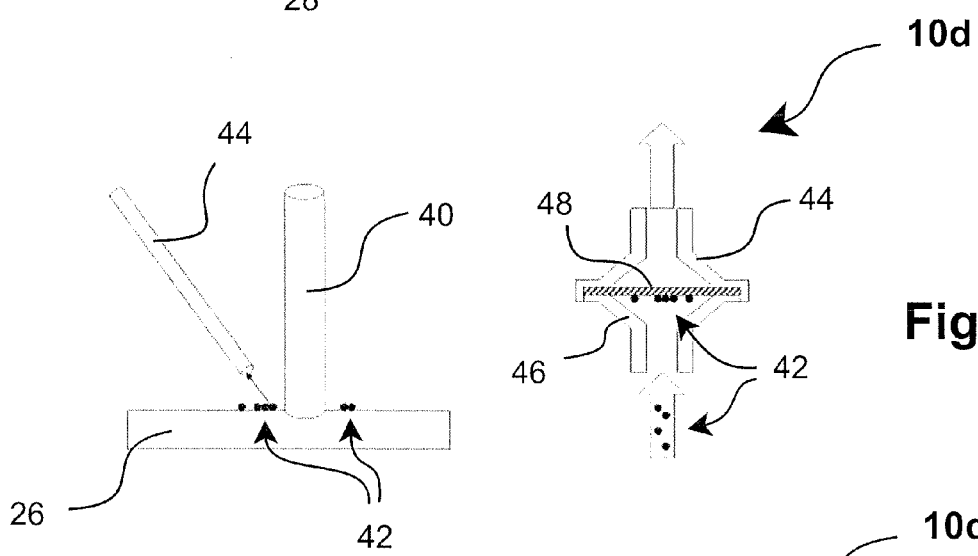
FIG. 5 shows a detection device for a fourth preferred embodiment of the invention.
Figure 6:
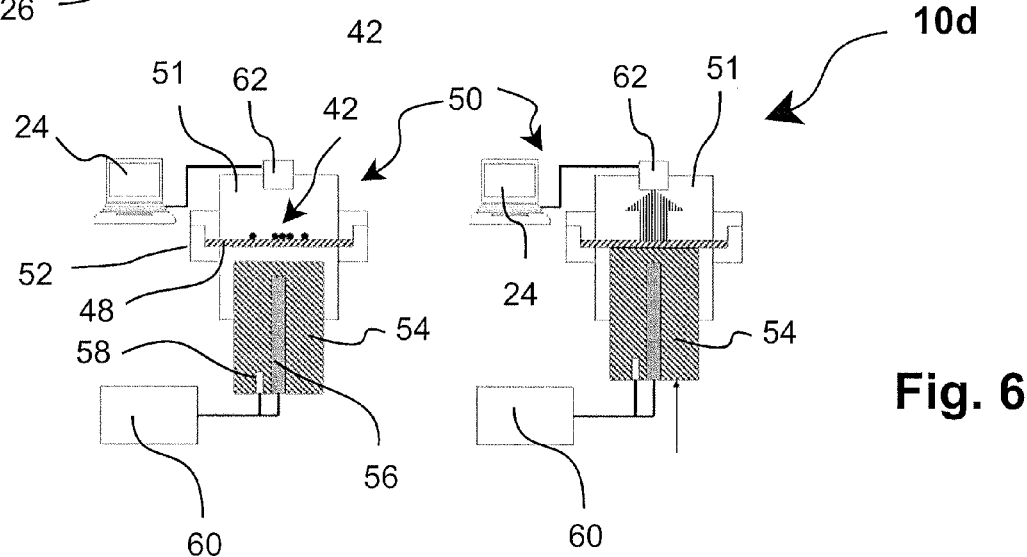
FIG. 6 shows a desorption device for a fourth preferred embodiment of the invention.

FIGS. 5 and 6 show a third preferred embodiment of a testing device 10d that differs from the previous designs in that the collection of the contaminated particles and the desorption of the contaminants are separate from one another. In FIG. 5 a composite component 26 is shown that is machined by means of an abrasive tool 40 (for example a grinding or milling device). In this case machining dust 42 is generated and is drawn off by means of an extractor device 44. A two-part filter housing 46 with an easily removable filter membrane 48, on which the machining dust particles 42 are collected, can be disposed in the extractor device. A suction pump (not shown) is located behind the filter housing 46.

FIG. 6 shows as part of the testing device 10d a desorption and detection unit 50, which comprises an analysis chamber 51 defined by a two-part housing 52 in which a dust-laden filter membrane 48 can be placed. The detection unit 50 also includes a movable heated punch 54 which with a heating element 56 and a thermometer 58 is connected for the purpose of temperature control to a thermostat 60 in order to ensure a constant temperature of the heated punch 54. The detection unit 50 comprises sensor array 62 with several gas detectors which are preferably constructed as MOX and/or NDIR sensors and/or humidity sensors.

In operation of the testing device 10d during the process of machining of the composite component 26 the machining dust is drawn off and concentrated on the filter membrane 48 (FIG. 5). Then the filter housing 46 is opened and the filter membrane 48 is removed and placed in the desorption and detection unit 50 (FIG. 6 left). Then the heated punch 54 is moved against the filter membrane 48 (FIG. 6 right), so that the contaminants present in the machining dust particles 42 can be desorbed at the elevated temperature and can be detected by means of the gas detectors 62.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof

LIST OF REFERENCE SIGNS 10a-d testing device
12 outer housing
14 heated punch
15 heating surface
16 heating element
18 thermometer
20 thermostat
22 sensor array
24 control device
26 composite component
28 scattered light chamber
30 halogen lamp
32 outer wall
34 radiation emitter
36 photodetectors
38 IR radiation
40 tool
42 machining dust
44 extractor device
46 filter housing
48 filter membrane
50 detection unit
51 analysis chamber
52 housing
54 heated punch
56 heating element
58 thermometer
60 thermostat
62 sensor array

The invention claimed is:

1. A device for testing a fibre-composite component, which is to be processed by means of bonding, for the presence of at least one substance out of a plurality of possible contaminants, the device comprising:

a surface heating device structurally configured to regionally heat an area of the fibre-composite component to be bonded in such a manner that contaminants are desorbed;

a sensor array with a plurality of sensors structurally configured to detect all contaminants in a gas phase; and a control device structurally configured to regulate the surface heating device, activate and readout the sensor array, and ascertain and signal detected contaminants, wherein the device is a mobile integral unit, wherein the surface heating device is a contact heating device.

2. The device as claimed in claim 1, wherein the surface heating device is a central heated punch surrounded by the sensor array, both of which are enclosed by an outer housing.

3. The device as claimed in claim 1, wherein the surface heating device is a central heated punch surrounded by an annular scattered light chamber with reflecting walls, and the device further comprise at least one IR light emitter configured to radiate into the scattered light chamber and several selective photodetectors are disposed in the wall of the scattered light chamber.

4. The device as claimed in claim 1, wherein that the surface heating device and the sensor array are disposed on different sides of the fibre-composite component.

5. The device as claimed in claim 1, wherein the sensor array comprises a number of metal oxide gas detectors (MOX) each of which is structurally configured to be sensitive to individual contaminants.

6. The device as claimed in claim 1, wherein the sensor array comprises at least one humidity sensor.

7. The device as claimed in claim 1, wherein the sensor array comprises at least one non-dispersive infrared sensor (NDIR).

8. The device as claimed in claim 1, wherein each of the plurality of sensors of the sensor array are selective for one or more of the following contaminants: surfactants, synthetic esters, alcohols, glycols, petrols, kerosenes, butyl phosphates, phenyl phosphates, phosphate esters, mineral oils, potassium acetates, sodium formiates, phosphates, silicates, water, moisture, butanones, methyl ethyl ketone, hydrocarbons, silicones, fluorocarbons, synthetic oils and lubricants.

9. The device as claimed in claim 1, wherein the fibre-composite component is an aircraft component.

10. A device for testing a fibre-composite component, which is to be processed by means of bonding, for the presence of at least one substance out of a plurality of possible contaminants, the device comprising:

a surface heating device structurally configured to regionally heat an area of the fibre-composite component to be bonded in such a manner that contaminants are desorbed;

an annular sensor array with a plurality of sensors structurally configured to detect all contaminants in a gas phase; and a control device structurally configured to regulate the surface heating device, activate and readout the annular sensor array, and ascertain and signal detected contaminants, wherein the device is a mobile integral unit, wherein the surface heating device is a heat radiating device centrally disposed and the annular sensor array surrounds a radiation range of the heat radiating device.

11. The device according to claim 10, wherein the device further comprises an optical thermometer, coupled to the control device, which is structurally arranged to measure a temperature of an irradiated region.

12. A device for testing a fibre-composite component, which is to be processed by means of bonding, for the presence of at least one substance out of a plurality of possible contaminants, the device comprising:

an abrasive tool configured to machine dust particles from the fibre-composite component;

an extractor device structurally configured to extract machining dust particles from the fibre-composite component;

a filter device structurally configured to collect the machining dust particles;

a desorption device structurally configured to thermally desorb contaminants from the machining dust particles;

a sensor array with a plurality of sensors structurally configured to detect all contaminants in a gas phase;

a control device structurally configured to regulate the desorption device, activate and readout the sensor array, and ascertain and signal detected contaminants.

13. The device as claimed in claim 12, wherein the desorption device has an analysis chamber structurally configured to be closed in a gas-tight manner and in which a linearly movable heated punch is arranged, which in a standby position is spaced apart from a sample membrane that can be brought into the analysis chamber spaced and in a working position can be brought towards the analysis chamber for desorption of the substances present in the dust particles, and the sensor array is disposed in a wall of the analysis chamber.

14. The device as claimed in claim 12, wherein the sensor array comprises a number of metal oxide gas detectors (MOX) each of which is structurally configured to be sensitive to individual contaminants.

15. The device as claimed in claim 12, the sensor array comprises at least one humidity sensor.

16. The device as claimed in claim 12, wherein the sensor array comprises at least one non-dispersive infrared sensor (NDIR).

17. The device as claimed in claim 12, wherein each of the plurality of sensors of the sensor array are selective for one or more of the following contaminants: surfactants, synthetic esters, alcohols, glycols, petrols, kerosenes, butyl phosphates, phenyl phosphates, phosphate esters, mineral oils, potassium acetates, sodium formiates, phosphates, silicates, water, moisture, butanones, methyl ethyl ketone, hydrocarbons, silicones, fluorocarbons, synthetic oils and lubricants.

18. The device as claimed in claim 12, wherein the fibre-composite component is an aircraft component.

19. A method for testing a fibre-composite component, which is to be processed by means of bonding, for the presence of at least one substance out of a plurality of possible contaminants, the method comprising:

regionally heating, by a surface heating device, an area of the fibre-composite component to be bonded in such a manner that contaminants are desorbed;

detecting, by a sensor array with a plurality of sensors structurally, all contaminants in a gas phase;

regulating, by a control device, the surface heating device;

activating and reading out, by the control device, the sensor array; and ascertaining and signalling, by the control device, contaminants detected by the sensor array, wherein the surface heating device is a contact heating device.

20. A method for testing a fibre-composite component, which is to be processed by means of bonding, for the presence of at least one substance out of a plurality of possible contaminants, the method comprising:
machining the fibre-composite component by an abrasive tool;
extracting, by an extractor device, machining dust particles from the fibre-composite component;
collecting, by a filter device, the machining dust particles;
thermally desorbing, by a desorption device, contaminants from the machining dust particles;
detecting, by a sensor array with a plurality of sensors, all contaminants in a gas phase;
regulating, by a control device, the desorption device;
activating and reading out, by the control device, the sensor array; and
ascertaining and signalling, by the control device, contaminants detected by the sensor array.

21. The method of claim 20, in which, after collecting the machining dust particles, further comprises:
moving the desorption device from a standby position spaced apart from the filter device into a working position against the filter device.

* * * * *